(12) United States Patent
Whiting et al.

(10) Patent No.: US 12,702,775 B2
(45) Date of Patent: Aug. 11, 2026

(54) PRESSURE RANGE ADJUSTMENT FOR RESPIRATORY THERAPY DEVICE

(71) Applicant: Fisher & Paykel Healthcare Limited, Auckland (NZ)

(72) Inventors: David Robin Whiting, Auckland (NZ); Simei Gomes Wysoski, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 54 days.

(21) Appl. No.: 18/665,312

(22) Filed: May 15, 2024

(65) Prior Publication Data

US 2024/0374848 A1 Nov. 14, 2024

Related U.S. Application Data

(63) Continuation of application No. 18/069,878, filed on Dec. 21, 2022, now Pat. No. 12,201,539, which is a (Continued)

(51) Int. Cl.

*A61M 16/00* (2006.01)
*A61B 5/00* (2006.01)

(Continued)

(52) U.S. Cl.

CPC ....... *A61M 16/0069* (2014.02); *A61B 5/0205* (2013.01); *A61B 5/087* (2013.01);

(Continued)

(58) Field of Classification Search

CPC ... A61B 5/02025; A61B 5/087; A61B 5/4818; A61B 5/4836; A61M 16/0057–0079

See application file for complete search history.

(56) References Cited

U.S. PATENT DOCUMENTS 8,261,742 B2 9/2012 Strothmann et al.
12,011,539 B2 6/2024 Whiting et al.

(Continued)

FOREIGN PATENT DOCUMENTS

WO WO 2005/077447 8/2005
WO WO 2006/133493 A1 12/2006

(Continued)

OTHER PUBLICATIONS

International Search Report for PCT/IB2015/051717 dated Jun. 29, 2015 in 6 pages.

(Continued)

*Primary Examiner* — LaToya M Louis
(74) *Attorney, Agent, or Firm* — Knobbe, Martens, Olson & Bear, LLP

(57) ABSTRACT

An automatic positive airway pressure (AutoPAP) therapy device can be configured such that the minimum and/or maximum pressures deliverable by the device can automatically change. The minimum and/or maximum pressures can change as a function of pressures delivered over the course of the current therapy session and/or over the course of prior therapy sessions. The minimum and/or maximum pressures can also change as a function of the presence, absence, type, severity, or length of sleep disordered breathing events (SDBE) detected by the device over the course of the current therapy session and/or over the course of prior therapy sessions.

20 Claims, 6 Drawing Sheets

Related U.S. Application Data continuation of application No. 15/124,298, filed as application No. PCT/IB2015/051717 on Mar. 10, 2015, now abandoned.

(60) Provisional application No. 61/950,746, filed on Mar. 10, 2014.

(51) Int. Cl.

| | |
|---|---|
| ***A61B 5/0205*** | (2006.01) |
| ***A61B 5/087*** | (2006.01) |
| ***A61M 16/06*** | (2006.01) |
| ***A61M 16/08*** | (2006.01) |
| ***A61M 16/10*** | (2006.01) |
| ***A61M 16/16*** | (2006.01) |
| *A61M 16/04* | (2006.01) |

(52) U.S. Cl.

CPC .......... *A61B 5/4818* (2013.01); *A61B 5/4836* (2013.01); *A61M 16/024* (2017.08); *A61M 16/06* (2013.01); *A61M 16/08* (2013.01); *A61M 16/109* (2014.02); *A61M 16/1095* (2014.02); *A61M 16/16* (2013.01); *A61M 2016/0027* (2013.01); *A61M 2016/0033* (2013.01); *A61M 2016/0039* (2013.01); *A61M 16/04* (2013.01); *A61M 16/0672* (2014.02); *A61M 2205/3303* (2013.01); *A61M 2205/3365* (2013.01); *A61M 2205/3375* (2013.01); *A61M 2205/3653* (2013.01); *A61M 2205/505* (2013.01); *A61M 2205/52* (2013.01); *A61M 2210/0618* (2013.01); *A61M 2230/06* (2013.01); *A61M 2230/10* (2013.01); *A61M 2230/202* (2013.01); *A61M 2230/205* (2013.01); *A61M 2230/43* (2013.01)

(56) References Cited

U.S. PATENT DOCUMENTS

| | | | |
|---|---|---|---|
| 2005/0241639 | A1 | 11/2005 | Zilberg |
| 2005/0268912 | A1 | 12/2005 | Norman et al. |
| 2006/0070625 | A1 | 4/2006 | Ayappa et al. |
| 2009/0107498 | A1 | 4/2009 | Plattner et al. |
| 2012/0145153 | A1 | 6/2012 | Bassin et al. |
| 2017/0014587 | A1 | 1/2017 | Whiting et al. |

FOREIGN PATENT DOCUMENTS

| | | | |
|---|---|---|---|
| WO | WO 2007/027888 | A1 | 3/2007 |
| WO | WO 2007/041182 | | 4/2007 |
| WO | WO 2007/140512 | A1 | 12/2007 |
| WO | WO 2009/149490 | A1 | 12/2009 |
| WO | WO 2013/144827 | | 10/2013 |
| WO | WO 2014/007659 | | 1/2014 |
| WO | WO 2014/150227 | A1 | 9/2014 |
| WO | WO 2015/136430 | | 9/2015 |

OTHER PUBLICATIONS

Written Opinion for PCT/IB2015/051717 dated Jun. 29, 2015 in 7 pages.

Examination Report in corresponding Australian Patent Application No. 2015228507, dated Dec. 4, 2018, in 4 pages.

Examination Report in corresponding Australian Patent Application No. 2015228507, dated Nov. 6, 2019, in 2 pages.

Examination Report in corresponding Australian Patent Application No. 2020201765, dated Nov. 5, 2020, in 3 pages.

Extended European Search Report in corresponding European Patent Application No. 20156443.2, dated Jul. 30, 2020, in 6 pages.

Koninklijke Philips Electronics N.V., Philips Respironics, REMstar Auto A-Flex User Manual, Publication Date Unknown, in 28 pages.

Philips Respironics, Intelligent Therapy: Philips Respironics System One 60 Series Presentation, Publication Date Unknown, in 57 pages.

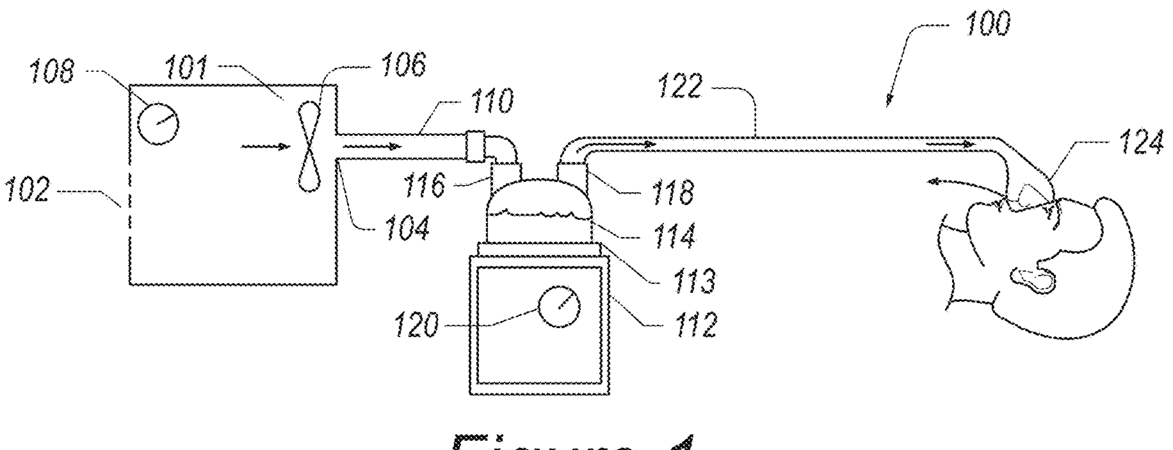
Figure 1
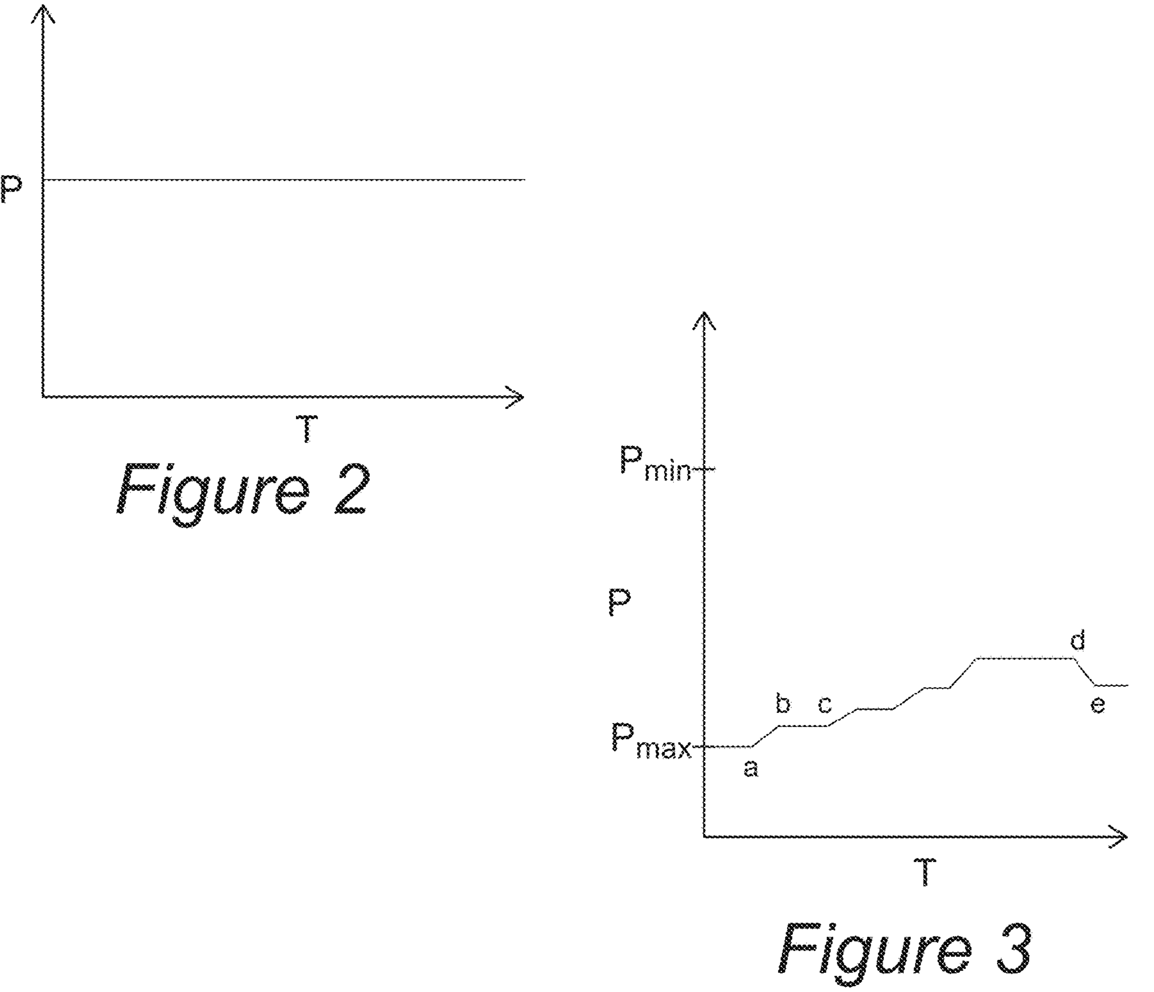
Figure 2
Figure 3

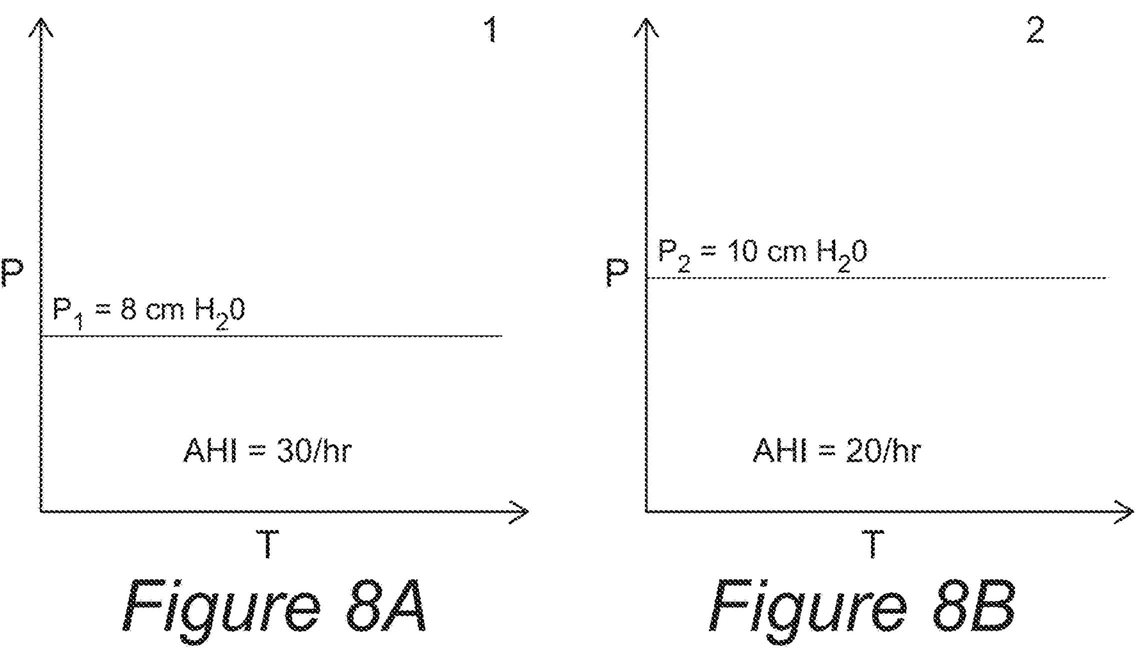
Figure 8A
Figure 8B
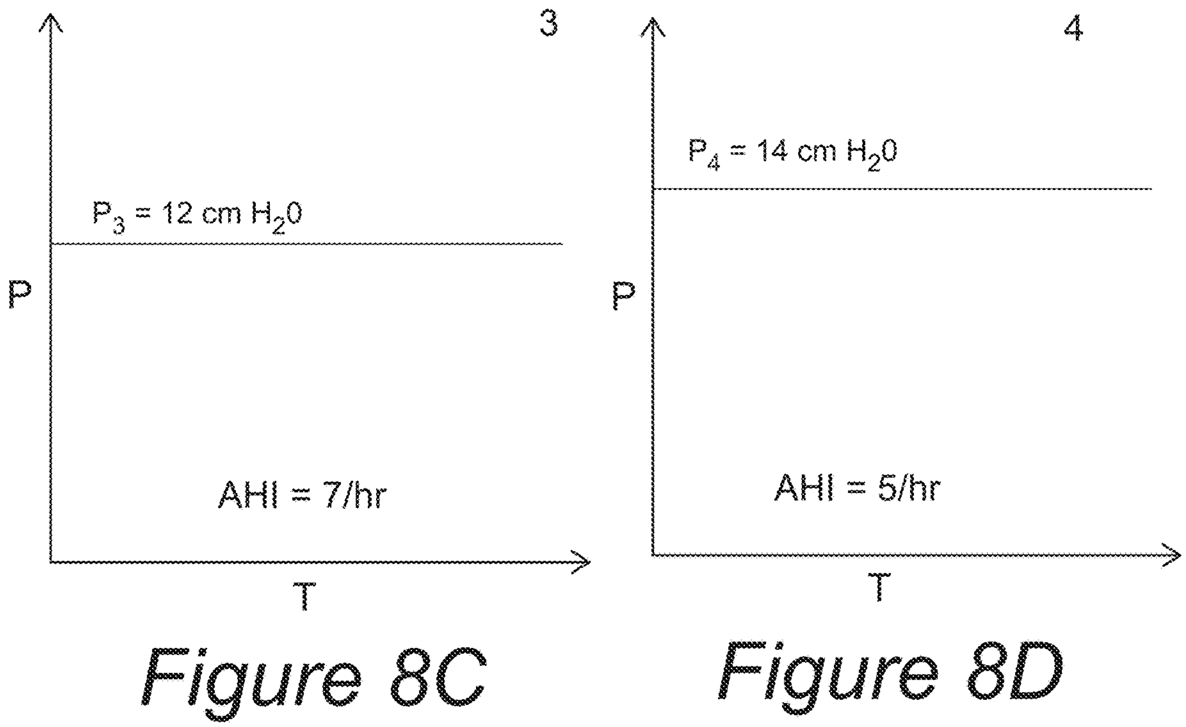
Figure 8C
Figure 8D

PRESSURE RANGE ADJUSTMENT FOR RESPIRATORY THERAPY DEVICE

INCORPORATION BY REFERENCE TO ANY PRIORITY APPLICATIONS

This application is a continuation of U.S. patent application Ser. No. 18/069,878, filed Dec. 21, 2022, entitled "PRESSURE RANGE ADJUSTMENT FOR RESPIRATORY THERAPY DEVICE," now U.S. Pat. No. 12,011,539, which is a continuation of U.S. patent application Ser. No. 15/124,298, filed Sep. 7, 2016, entitled "PRESSURE RANGE ADJUSTMENT FOR RESPIRATORY THERAPY DEVICE," which is a national phase of PCT/IB2015/051717, filed Mar. 10, 2015, entitled "PRESSURE RANGE ADJUSTMENT FOR RESPIRATORY THERAPY DEVICE," which claims priority to U.S. Prov. Pat. App. 61/950,746, filed Mar. 10, 2014, entitled "PRESSURE RANGE ADJUSTMENT FOR RESPIRATORY THERAPY DEVICE." The application identified in this paragraph is incorporated by reference herein in its entirety. Any and all applications for which a foreign or domestic priority claim is identified in the Application Data Sheet as filed with the present application are hereby incorporated by reference under 37 CFR 1.57.

FIELD OF THE DISCLOSURE

The present disclosure generally relates to respiratory therapy devices. More particularly, the present disclosure relates to control systems for use with respiratory therapy devices.

BACKGROUND

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other physiological complication. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that may reduce the frequency and/or duration of apneas, hypopneas, and/or flow limitations. This therapy may be delivered by using a positive airway pressure device (PAP device) to propel a pressurized stream of air through a conduit to a patient through an interface or mask located on the face of the patient. The stream of air may be heated to near body temperature. The stream of air may be humidified. The humidification may be performed by forcing the stream of air to travel through a respiratory humidifier containing water and a heater for heating the water. In such a system the heater encourages the evaporation of the water, which in turn partially or fully imbues the stream of air with moisture and/or heat. This moisture and/or heat may help to ameliorate discomfort that may arise from the use of unhumidified PAP therapy.

In respiratory therapy methods involving administration of pressurized respiratory gases to treat obstructive sleep apnea, it is known to use constant positive airway pressure therapy, in which the pressure delivered over the course of a therapy session remains constant. An example of such a therapy is shown in FIG. 2 as a pressure (P) versus time (T) graph. In some situations, bi-level PAP therapy (also known as BiPAP therapy) may be used to treat OSA. Bi-level PAP therapy may refer to a PAP therapy in which a PAP device may be used to deliver a first pressure at or around a detection of an inhalation of a patient (e.g., an inhalation positive airway pressure or IPAP) and deliver a second pressure at or around a detection of an exhalation of the patient (e.g., an exhalation positive airway pressure or EPAP). To provide patient comfort, the second pressure may be lower than the first pressure. In some situations, the PAP device may reduce the pressure delivered from a therapeutic level to a sub-therapeutic level upon determination of a wakeful state of the patient and increase the pressure delivered from a sub-therapeutic level to a therapeutic level upon determination of an asleep state of the patient. In some situations, it is desirable to configure a PAP device in such a way that the pressure delivered is automatically adjusted over the course of a therapy session to match the needs of the patient. It is believed that utilizing high pressures only when the patient requires high pressure therapy for a respiratory disorder can improve the comfort of the therapy. Accordingly, an automatically adjusting PAP device (AutoPAP device) capable of adjusting the delivered pressure in such a way that the delivered pressure may increase or decrease upon the detection of the presence or absence of symptoms of a respiratory disorder may be provided. An example of AutoPAP therapy is shown in FIG. 3 as a pressure versus time graph. As can be seen, the AutoPAP device may initially start the patient at a predetermined pressure (for example, $P_{min}$ as shown in FIG. 1) and increase the delivered pressure upon detection of a symptom of a respiratory disorder (for example, as shown at point a or point c in FIG. 3). The AutoPAP device may also decrease the delivered pressure upon detection of the absence of symptoms of a respiratory disorder for a period of time (for example, as shown at point d of FIG. 3). In such an AutoPAP device, in at least one mode the range of pressures that the device may deliver may be bounded by a minimum pressure level defining the lowest pressure deliverable by the device and a maximum pressure level defining the highest pressure deliverable by the device. In many cases, the minimum and/or maximum pressures are prescribed by a medical professional, and the device is likewise configured by the professional or a medical device dealer.

SUMMARY

In many cases, when a physician wishes to prescribe AutoPAP therapy for a patient with obstructive sleep apnea or another condition treatable with PAP therapy, there is some difficulty in deciding on the correct pressure range for the AutoPAP device. If the pressure range selected is too large, for example 4 cm $H_2O$ to 18 cm $H_2O$, the minimum pressure of the range (e.g., 4 cm $H_2O$) may be too low to be therapeutically effective, and the maximum pressure of the range (e.g., 18 cm $H_2O$) may be greater than required for maximal therapeutic benefit and/or too high for optimal patient comfort. If the pressure range selected is too small, for example 10 cm $H_2O$ to 12 cm $H_2O$, the pressures administered over the entire range may be too high for comfort or too low to be effective, and/or the device may have a limited ability to compensate for the onset of respiratory disorder symptoms. Faced with such a problem, it is possible that the physician may initially prescribe AutoPAP therapy with a large pressure range, and have the patient use an AutoPAP device with this pressure range for a trial period, e.g., one week. During use, the AutoPAP device may record the pressures delivered by the device during the trial period and the physician may, for example, examine the recorded data during a subsequent visit with the patient. The physician may then use his/her judgment to set an appropriate range of pressures for the patient based on the data available.

In such a scenario, the physician spends additional time with the patient and/or the patient's records, inconveniencing the physician and increasing the burden on public and/or private healthcare systems. Accordingly, it is an object of the disclosure to provide an improved PAP system that might solve one or more of the above problems, or at least provide the public with a useful choice.

Thus, in accordance with at least one of the embodiments disclosed herein, a respiratory therapy system is disclosed. The respiratory therapy system is configured to adjust the operational pressure range of the system based on sensed information about the treatment of the patient as described herein. The respiratory therapy system may comprise a flow generator. The respiratory therapy system may comprise a sensor. The sensor may be adapted to measure at least one characteristic capable of being used to determine one or more traits of a sleep-disordered breathing event (SDBE) of the patient. The respiratory therapy system may comprise a controller. The controller may be configured to receive the at least one characteristic measured by the sensor. The controller may be configured to analyze the at least one characteristic. The at least one characteristic may be analyzed to determine one or more traits of an SDBE of the patient. The controller may control the flow generator to maintain or adjust a pressure delivered by the flow generator between a minimum and a maximum pressure, inclusive. The maintaining or adjusting may be at least in part based on the determined one or more traits of an SDBE. The minimum and/or maximum pressures may be adjusted in response to one or more parameters recorded during the course of the current therapy session and/or one or more previous or past therapy sessions. The parameters may include at least one of the following: the pressure delivered and the one or more traits of the SDBE. In some configurations, the controller may control the flow generator to maintain or adjust the pressure delivered by the flow generator between a minimum and a maximum pressure, inclusive, on an event-by-event basis. In other words, the controller may react to individual SDBEs as they are detected. In some configurations, the controller may make the decision to change or not change the minimum and/or maximum pressures on a session-by-session basis, a time period-by-time period basis, a night-by-night basis, or on some other basis.

In some configurations, the characteristics capable of being used to determine the one or more traits of an SDBE may include one or more of the following: gas pressure (e.g. delivered gas pressure), gas flow (e.g. delivered gas flow), sound, flow generator current (e.g. flow generator motor driving current), flow generator speed (e.g. flow generator motor speed), flow generator motor torque, motion (e.g. patient motion), tidal volume, heart rate, lung volume, electroencephalograph signal, EEG signal, EKG/ECG signal, breath composition, blood oxygen concentration, and blood CO2 concentration. The traits of an SDBE may include one or more of the following: the presence of an SDBE, the absence of an SDBE, the type of SDBE, the severity of SDBE, the length of the SDBE, and the latency of the SDBE.

The minimum pressure and/or maximum pressure may be adjusted in response to the pressure delivered during the course of the present therapy session. The minimum pressure and/or maximum pressure may be adjusted in response to the pressure(s) delivered during the course of one or more previous therapy sessions. The minimum pressure and/or maximum pressure may be adjusted in response to both the pressure delivered during the course of the present therapy session and the pressure(s) delivered over the course of one or more previous therapy sessions. In some configurations, the delivered pressure at which the patient spent a percentage of time at or below over the course of one or more previous therapy sessions may be recorded. The minimum and/or maximum pressures may be adjusted to a function of the recorded pressure.

In some configurations, if the patient spends a percentage of time at the maximum pressure greater than or equal to a first or threshold percentage of time at the maximum pressure over the course of one or more previous therapy sessions, the maximum pressure may be increased. The threshold percentage of time may be predetermined. In some configurations, if the patient spends a percentage of time at the maximum pressure less than or equal to a threshold percentage of time at the maximum pressure over the course of one or more previous therapy sessions, the maximum pressure may be decreased. The threshold percentage of time may be predetermined. In some configurations, if the patient experiences a number of pressure increases at or near the minimum pressure that is greater than or equal to a predetermined number over a predetermined period of time, the minimum pressure may be increased.

Additionally, in accordance with at least one of the embodiments disclosed herein, a method for delivering a respiratory therapy is disclosed. A pressurized gas may be delivered to a patient. At least one characteristic capable of being used to determine one or more traits of a sleep-disordered breathing event (SDBE) may be measured. The at least one characteristic may be analyzed to determine the one or more traits of a sleep-disordered breathing event of the patient. The pressure of the pressurized gas delivered to the patient may be maintained or adjusted between a minimum pressure and a maximum pressure, inclusive. The pressure may be maintained or adjusted at least in part based on the determined one or more traits of an SDBE. The minimum and/or maximum pressures may be adjusted in response to one or more parameters recorded during the course of the current therapy session and/or one or more previous or past therapy sessions. The parameters may include at least one of the following: the pressure delivered and the one or more traits of the SDBE. In some configurations, the decision to maintain or adjust the pressure delivered between a minimum and a maximum pressure, inclusive, may be made on an event-by-event basis. In other words, a decision may be made to react to individual SDBEs as they are detected. In some configurations, a decision may be made to change or not change the minimum and/or maximum pressures on an (SDBE) event-by-event basis, a session-by-session basis, a time period-by-time period basis, a night-by-night basis, or on some other basis.

In some configurations, the characteristics capable of being used to determine the one or more traits of an SDBE may include one or more of the following: gas pressure (e.g. delivered gas pressure), gas flow (e.g. delivered gas flow), sound, flow generator current (e.g. flow generator motor driving current), flow generator speed (e.g. flow generator motor speed), flow generator motor torque, motion (e.g. patient motion), tidal volume, heart rate, lung volume, EEG signal, EKG/ECG signal, breath composition, blood oxygen concentration, and blood $CO_2$ concentration. The traits of an SDBE may include one or more of the following: the presence of an SDBE, the absence of an SDBE, the type of SDBE, the severity of SDBE, the length of the SDBE, and the latency of the SDBE.

The minimum pressure and/or maximum pressure may be adjusted in response to the pressure delivered during the course of the present therapy session. The minimum pressure and/or maximum pressure may be adjusted in response to the pressure(s) delivered during the course of one or more previous therapy sessions. The minimum pressure and/or maximum pressure may be adjusted in response to both the pressure delivered during the course of the present therapy session and the pressure(s) delivered over the course of one or more previous therapy sessions. In some configurations, the delivered pressure which the patient spent a percentage of time at or below over the course of one or more previous therapy sessions may be recorded. The minimum and/or maximum pressures may be adjusted to a function of the recorded pressure.

In some configurations, if the patient spends a percentage of time at the maximum pressure greater than or equal to a first or threshold percentage of time at the maximum pressure over the course of one or more previous therapy sessions, the maximum pressure may be increased. The threshold percentage of time may be predetermined. In some configurations, if the patient spends a percentage of time at the maximum pressure less than or equal to a threshold percentage of time at the maximum pressure over the course of one or more previous therapy sessions, the maximum pressure may be decreased. The percentage of time may be predetermined. In some configurations, if the patient experiences a number of pressure increases at or near the minimum pressure that is greater than or equal to a predetermined number over a predetermined period of time, the minimum pressure may be increased.

In accordance with at least some configurations disclosed herein is a method of delivering a respiratory therapy comprising: delivering a pressurized gas to a patient with a flow generator, measuring with a sensor at least one characteristic capable of being used to determine one or more traits of a sleep-disordered breathing event (SDBE) of the patient, determining with a hardware controller the one or more traits of the SDBE of the patient by analyzing the at least one characteristic, repeatedly adjusting a pressure window comprising a minimum pressure limit and a maximum pressure limit in response to one or more parameters measured during the course of the current therapy session and/or one or more previous therapy sessions, the one or more parameters including at least pressure delivered or the determined one or more traits of the SDBE; and controlling the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the characteristics capable of being used to determine the one or more traits of the SDBE include one or more of the following: gas pressure, gas flow, sound, flow generator current, flow generator speed, flow generator motor torque, motion, tidal volume, heart rate, lung volume, EEG signal, breath composition, blood oxygen concentration, and blood $CO_2$ concentration.

In some configurations the traits of the SDBE include one or more of the following: presence of the SDBE, absence of the SDBE, type of SDBE, severity of the SDBE, length of the SDBE, and latency of the SDBE.

In some configurations a decision may be made to maintain or adjust the pressure delivered between the minimum pressure limit and the maximum pressure limit, inclusive, on an event-by-event basis.

In some configurations the therapy sessions comprise only the current therapy session.

In some configurations the therapy sessions comprise only one or more previous therapy sessions.

In some configurations the therapy sessions comprise both the current therapy session and one or more previous therapy sessions.

In some configurations the minimum pressure limit or the maximum pressure limit is adjusted in response to the pressure delivered during the course of the current therapy session and/or one or more previous therapy sessions.

In some configurations the minimum pressure limit or the maximum pressure limit is adjusted in response to the pressure delivered during one or more previous therapy sessions.

In some configurations the delivered pressure at which the patient spent a percentage of time at or below over the course of one or more previous therapy sessions is recorded, and the minimum pressure limit or the maximum pressure limit is adjusted to a function of the recorded pressure.

In some configurations if the patient spends a time at the maximum pressure limit that is greater than or equal to a threshold percentage of time at the maximum pressure limit over the course of one or more previous therapy sessions, the maximum pressure limit is increased.

In some configurations if the patient spends a time at the maximum pressure limit that is less than or equal to a threshold percentage of time at the maximum pressure limit over the course of one or more previous therapy sessions, the maximum pressure limit is decreased.

In some configurations if the patient experiences a number of delivered pressure increases greater than a predetermined number over a predetermined period of time at or near the minimum pressure limit, the minimum pressure limit is increased.

In some configurations the respiratory therapy comprises automatic positive airway pressure therapy.

In some configurations the minimum pressure limit or the maximum pressure limit is adjusted during a therapy session.

In some configurations both the minimum pressure limit and the maximum pressure limit are adjusted during the therapy session.

In accordance with at least some configurations disclosed herein is a non-transitory computer readable medium configured to store executable instructions for a method of delivering a respiratory therapy, the executable instructions comprising: controlling a flow generator to deliver a pressurized gas to a patient, receiving from a sensor measurements of at least one characteristic capable of being used to determine one or more traits of a sleep-disordered breathing event (SDBE) of the patient, determining with a hardware controller the one or more traits of the SDBE of the patient by analyzing the at least one characteristic, repeatedly adjusting a pressure window comprising a minimum pressure limit and a maximum pressure limit in response to one or more parameters measured during the course of the current therapy session and/or one or more previous therapy sessions, the one or more parameters including at least pressure delivered or the determined one or more traits of the SDBE; and controlling the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the characteristics capable of being used to determine the one or more traits of the SDBE include one or more of the following: gas pressure, gas flow, sound, flow generator current, flow generator speed, flow generator motor torque, motion, tidal volume, heart rate, lung volume, EEG signal, breath composition, blood oxygen concentration, and blood CO2 concentration.

In some configurations the traits of the SDBE include one or more of the following: presence of the SDBE, absence of the SDBE, type of SDBE, severity of the SDBE, length of the SDBE, and latency of the SDBE.

In some configurations a decision may be made to maintain or adjust the pressure delivered between the minimum pressure limit and the maximum pressure limit, inclusive, on an event-by-event basis.

In some configurations the therapy sessions comprise only the current therapy session.

In some configurations the therapy sessions comprise only one or more previous therapy sessions.

In some configurations the therapy sessions comprise both the current therapy session and one or more previous therapy sessions.

In some configurations the minimum pressure limit or the maximum pressure limit is adjusted in response to the pressure delivered during the course of the current therapy session and/or one or more previous therapy sessions.

In some configurations the minimum pressure limit or the maximum pressure limit is adjusted in response to the pressure delivered during one or more previous therapy sessions.

In some configurations the delivered pressure at which the patient spent a percentage of time at or below over the course of one or more previous therapy sessions is recorded, and the minimum pressure limit or the maximum pressure limit is adjusted to a function of the recorded pressure.

In some configurations if the patient spends a time at the maximum pressure limit that is greater than or equal to a threshold percentage of time at the maximum pressure limit over the course of one or more previous therapy sessions, the maximum pressure limit is increased.

In some configurations if the patient spends a time at the maximum pressure limit that is less than or equal to a threshold percentage of time at the maximum pressure limit over the course of one or more previous therapy sessions, the maximum pressure limit is decreased.

In some configurations if the patient experiences a number of delivered pressure increases greater than a predetermined number over a predetermined period of time at or near the minimum pressure limit, the minimum pressure limit is increased.

In some configurations the respiratory therapy comprises automatic positive airway pressure therapy.

In some configurations the minimum pressure limit or the maximum pressure limit is adjusted during a therapy session.

In some configurations both the minimum pressure limit and the maximum pressure limit are adjusted during the therapy session.

In accordance with at least some configurations disclosed herein is a respiratory therapy system comprising: a flow generator adapted to provide pressurized gases to a patient, a sensor adapted to measure at least one characteristic capable of being used to determine one or more traits of a sleep-disordered breathing event (SDBE) of the patient, and a hardware controller configured to: receive the at least one characteristic measured by the sensor, determine the one or more traits of the SDBE of the patient by analyzing the at least one characteristic, adjust a pressure window for a first therapy session, the pressure window comprising a minimum pressure limit and a maximum pressure limit, wherein the hardware controller adjusts the pressure window in response to one or more parameters measured during the course of one or more second therapy sessions, the one or more parameters including at least the determined one or more traits of the SDBE; and control the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the characteristics capable of being used to determine the one or more traits of the SDBE include one or more of the following: gas pressure, gas flow, sound, flow generator current, flow generator speed, flow generator motor torque, motion, tidal volume, heart rate, lung volume, EEG signal, breath composition, blood oxygen concentration, and blood CO2 concentration.

In some configurations the first therapy session is a current therapy session.

In some configurations the first therapy session is a future therapy session.

In some configurations the one or more second therapy sessions are past therapy sessions, wherein the one or more parameters measured during the course of one or more second therapy sessions comprises historical data measured for the patient.

In accordance with at least some configurations disclosed herein is a method of providing respiratory therapy, the method comprising: delivering pressurized gases to a patient using a flow generator; measuring with a sensor at least one characteristic capable of being used to determine one or more traits of a sleep-disordered breathing event (SDBE) of the patient; determining the one or more traits of the SDBE of the patient by analyzing the at least one characteristic; adjusting a pressure window for a first therapy session, the pressure window comprising a minimum pressure limit and a maximum pressure limit, wherein the hardware controller adjusts the pressure window in response to one or more parameters measured during the course of one or more second therapy sessions, the one or more parameters including at least the determined one or more traits of the SDBE; and controlling the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the characteristics capable of being used to determine the one or more traits of the SDBE include one or more of the following: gas pressure, gas flow, sound, flow generator current, flow generator speed, flow generator motor torque, motion, tidal volume, heart rate, lung volume, EEG signal, breath composition, blood oxygen concentration, and blood CO2 concentration.

In some configurations the first therapy session is a current therapy session.

In some configurations the first therapy session is a future therapy session.

In some configurations the one or more second therapy sessions are past therapy sessions, wherein the one or more parameters measured during the course of one or more second therapy sessions comprises historical data measured for the patient.

In accordance with at least some configurations disclosed herein is a non-transitory computer readable medium configured to store executable instructions for a method of delivering a respiratory therapy, the executable instructions comprising: delivering pressurized gases to a patient using a flow generator; measuring with a sensor at least one characteristic capable of being used to determine one or more traits of a sleep-disordered breathing event (SDBE) of the patient; determining the one or more traits of the SDBE of the patient by analyzing the at least one characteristic, adjusting a pressure window for a first therapy session, the pressure window comprising a minimum pressure limit and a maximum pressure limit, wherein the hardware controller adjusts the pressure window in response to one or more parameters measured during the course of one or more second therapy sessions, the one or more parameters including at least the determined one or more traits of the SDBE; and controlling the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the characteristics capable of being used to determine the one or more traits of the SDBE include one or more of the following: gas pressure, gas flow, sound, flow generator current, flow generator speed, flow generator motor torque, motion, tidal volume, heart rate, lung volume, EEG signal, breath composition, blood oxygen concentration, and blood CO2 concentration.

In some configurations the first therapy session is a current therapy session.

In some configurations the first therapy session is a future therapy session.

In some configurations the one or more second therapy sessions are past therapy sessions, wherein the one or more parameters measured during the course of one or more second therapy sessions comprises historical data measured for the patient.

In accordance with at least some configurations disclosed herein is a respiratory therapy system comprising: a flow generator adapted to provide pressurized gases to a patient, a sensor adapted to measure at least one characteristic capable of being used to determine one or more traits of a sleep-disordered breathing event (SDBE) of the patient, and a hardware controller configured to: receive the at least one characteristic measured by the sensor, determine the one or more traits of the SDBE of the patient by analyzing the at least one characteristic, repeatedly adjust a pressure window for a first therapy session, the pressure window comprising a minimum pressure limit and a maximum pressure limit, wherein the hardware controller adjusts the pressure window in response to one or more parameters measured during the course of one or more second therapy sessions, the one or more parameters including pressure delivered to the patient; and control the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the first therapy session is a current therapy session.

In some configurations the first therapy session is a future therapy session.

In some configurations the one or more second therapy sessions are previous therapy sessions, wherein the one or more parameters measured during the course of one or more second therapy sessions comprises historical data measured for the patient.

In some configurations the minimum pressure limit or the maximum pressure limit is adjusted in response to the pressure delivered during the one or more previous therapy sessions.

In some configurations the delivered pressure at which the patient spent a percentage of time at or below over the course of one or more previous therapy sessions is recorded, and the minimum pressure limit or the maximum pressure limit is adjusted to a function of the recorded pressure.

In some configurations if the patient spends a time at the maximum pressure limit that is greater than or equal to a threshold percentage of time at the maximum pressure limit over the course of one or more previous therapy sessions, the maximum pressure limit is increased.

In some configurations if the patient spends a time at the maximum pressure limit that is less than or equal to a threshold percentage of time at the maximum pressure limit over the course of one or more previous therapy sessions, the maximum pressure limit is decreased.

In some configurations if the patient experiences a number of delivered pressure increases greater than a predetermined number over a predetermined period of time at or near the minimum pressure limit, the minimum pressure limit is increased.

In accordance with at least some configurations disclosed herein is a method for providing respiratory therapy to a patient, the method comprising: delivering pressurized gases to a patient using a flow generator; measuring with a sensor at least one characteristic capable of being used to determine one or more traits of a sleep-disordered breathing event (SDBE) of the patient; determining the one or more traits of the SDBE of the patient by analyzing the at least one characteristic; repeatedly adjusting a pressure window for a first therapy session, the pressure window comprising a minimum pressure limit and a maximum pressure limit, wherein the hardware controller adjusts the pressure window in response to one or more parameters measured during the course of one or more second therapy sessions, the one or more parameters including pressure delivered to the patient; and controlling the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the first therapy session is a current therapy session.

In some configurations the first therapy session is a future therapy session.

In some configurations the one or more second therapy sessions are previous therapy sessions, wherein the one or more parameters measured during the course of one or more second therapy sessions comprises historical data measured for the patient.

In some configurations the one or more second therapy sessions are previous therapy sessions, wherein the one or more parameters measured during the course of one or more second therapy sessions comprises historical data measured for the patient.

In some configurations the minimum pressure limit or the maximum pressure limit is adjusted in response to the pressure delivered during the one or more previous therapy sessions.

In some configurations the delivered pressure at which the patient spent a percentage of time at or below over the course of one or more previous therapy sessions is recorded, and the minimum pressure limit or the maximum pressure limit is adjusted to a function of the recorded pressure.

In some configurations if the patient spends a time at the maximum pressure limit that is greater than or equal to a threshold percentage of time at the maximum pressure limit over the course of one or more previous therapy sessions, the maximum pressure limit is increased.

In some configurations if the patient spends a time at the maximum pressure limit that is less than or equal to a threshold percentage of time at the maximum pressure limit over the course of one or more previous therapy sessions, the maximum pressure limit is decreased.

In some configurations if the patient experiences a number of delivered pressure increases greater than a predetermined number over a predetermined period of time at or near the minimum pressure limit, the minimum pressure limit is increased.

In accordance with at least some configurations disclosed herein is a non-transitory computer readable medium configured to store executable instructions for a method of delivering a respiratory therapy, the executable instructions comprising: delivering pressurized gases to a patient using a flow generator; measuring with a sensor at least one characteristic capable of being used to determine one or more traits of a sleep-disordered breathing event (SDBE) of the patient; determining the one or more traits of the SDBE of the patient by analyzing the at least one characteristic; repeatedly adjusting a pressure window for a first therapy session, the pressure window comprising a minimum pressure limit and a maximum pressure limit, wherein the hardware controller adjusts the pressure window in response to one or more parameters measured during the course of one or more second therapy sessions, the one or more parameters including pressure delivered to the patient; and controlling the flow generator to deliver pressurized gases, the pressure of the pressurized gases being at least in part based on the determined one or more traits of the SDBE, and the pressure of the pressurized gases being greater than or equal to the minimum pressure limit and less than or equal to the maximum pressure limit, wherein the minimum pressure limit is less than the maximum pressure limit.

In some configurations the first therapy session is a current therapy session.

In some configurations the first therapy session is a future therapy session.

In some configurations the one or more second therapy sessions are previous therapy sessions, wherein the one or more parameters measured during the course of one or more second therapy sessions comprises historical data measured for the patient.

In some configurations the one or more second therapy sessions are previous therapy sessions, wherein the one or more parameters measured during the course of one or more second therapy sessions comprises historical data measured for the patient.

In some configurations the minimum pressure limit or the maximum pressure limit is adjusted in response to the pressure delivered during the one or more previous therapy sessions.

In some configurations the delivered pressure at which the patient spent a percentage of time at or below over the course of one or more previous therapy sessions is recorded, and the minimum pressure limit or the maximum pressure limit is adjusted to a function of the recorded pressure.

In some configurations the patient spends a time at the maximum pressure limit that is greater than or equal to a threshold percentage of time at the maximum pressure limit over the course of one or more previous therapy sessions, the maximum pressure limit is increased.

In some configurations if the patient spends a time at the maximum pressure limit that is less than or equal to a threshold percentage of time at the maximum pressure limit over the course of one or more previous therapy sessions, the maximum pressure limit is decreased.

In some configurations if the patient experiences a number of delivered pressure increases greater than a predetermined number over a predetermined period of time at or near the minimum pressure limit, the minimum pressure limit is increased.

In accordance with at least some configurations disclosed herein is a respiratory therapy system comprising: a flow generator adapted to provide pressurized gases to a patient, a sensor adapted to measure at least one characteristic capable of being used to determine one or more traits of a sleep-disordered breathing event (SDBE) of the patient, and a hardware controller configured to: in a first therapy mode, control the flow generator to deliver pressurized gases at a first pressure level for a first time period and to deliver pressurized gases at a second pressure level for a second time period; determine for each of the first time period and the second time period a sleep index based on one or more traits of the SDBE of the patient by analyzing the at least one characteristic; and determine a pressure window of a second therapy mode, the pressure window comprising a minimum pressure limit and a maximum pressure limit, wherein the hardware controller determines the pressure window by using a continuous function that associates a sleep index with a pressure level and by using the continuous function to determine a tailored pressure level that achieves a targeted sleep index; and defining the minimum pressure limit and the maximum pressure limit of the pressure window based on the tailored pressure level; wherein the minimum pressure limit is less than the maximum pressure limit.

In some configurations the targeted sleep index is an optimization utilizing the continuous function.

In some configurations the targeted sleep index is a minimum of the continuous function.

In some configurations the targeted sleep index is a maximum of the continuous function.

In accordance with at least some configurations disclosed herein is a method of providing respiratory therapy, the method comprising: delivering pressurized gases to a patient using a flow generator; measuring with a sensor at least one characteristic capable of being used to determine one or more traits of a sleep-disordered breathing event (SDBE) of the patient; in a first therapy mode, controlling the flow generator to deliver pressurized gases at a first pressure level for a first time period and to deliver pressurized gases at a second pressure level for a second time period; determining for each of the first time period and the second time period a sleep index based on one or more traits of the SDBE of the patient by analyzing the at least one characteristic; determining a pressure window of a second therapy mode, the pressure window comprising a minimum pressure limit and a maximum pressure limit, wherein the hardware controller determines the pressure window by using a continuous function that associates a sleep index with a pressure level and by using the continuous function to determine a tailored pressure level that achieves a targeted sleep index; and defining the minimum pressure limit and the maximum pressure limit of the pressure window based on the tailored pressure level; wherein the minimum pressure limit is less than the maximum pressure limit.

In some configurations the targeted sleep index is an optimization utilizing the continuous function.

In some configurations the targeted sleep index is a minimum of the continuous function.

In some configurations the targeted sleep index is a maximum of the continuous function.

In accordance with at least some configurations disclosed herein is a non-transitory computer readable medium configured to store executable instructions for a method of delivering a respiratory therapy, the executable instructions comprising: delivering pressurized gases to a patient using a flow generator; measuring with a sensor at least one characteristic capable of being used to determine one or more traits of a sleep-disordered breathing event (SDBE) of the patient; in a first therapy mode, controlling the flow generator to deliver pressurized gases at a first pressure level for a first time period and to deliver pressurized gases at a second pressure level for a second time period; determining for each of the first time period and the second time period a sleep index based on one or more traits of the SDBE of the patient by analyzing the at least one characteristic; determining a pressure window of a second therapy mode, the pressure window comprising a minimum pressure limit and a maximum pressure limit, wherein the hardware controller determines the pressure window by using a continuous function that associates a sleep index with a pressure level and by using the continuous function to determine a tailored pressure level that achieves a targeted sleep index; and defining the minimum pressure limit and the maximum pressure limit of the pressure window based on the tailored pressure level; wherein the minimum pressure limit is less than the maximum pressure limit.

In some configurations the targeted sleep index is an optimization utilizing the continuous function.

In some configurations the targeted sleep index is a minimum of the continuous function.

In some configurations the targeted sleep index is a maximum of the continuous function.

BRIEF DESCRIPTION OF THE DRAWINGS

Specific embodiments and modifications thereof will become apparent to those skilled in the art from the detailed description herein having reference to the figures that follow, of which:

FIG. 1 shows a schematic diagram of a respiratory therapy system.

FIG. 2 shows a pressure versus time graph demonstrating an example of constant positive airway pressure therapy.

FIG. 3 shows a pressure versus time graph demonstrating an example of automatic positive airway pressure (AutoPAP or APAP) therapy.

FIGS. 8A-8D show a set of pressure versus time graphs demonstrating several therapy sessions of constant PAP therapy, wherein the pressure used for each of the several therapy sessions is different.

DETAILED DESCRIPTION OF THE PREFERRED EMBODIMENT

Figure 4:
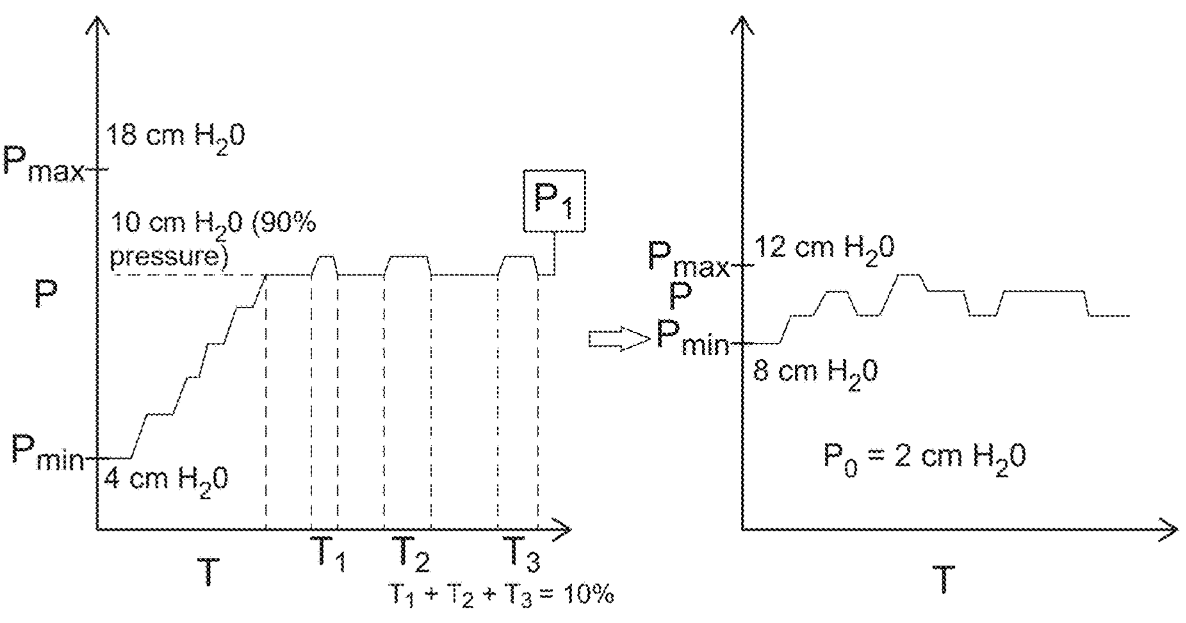
FIG. 4 shows a pair of pressure versus time graphs demonstrating an example of AutoPAP therapy wherein the minimum and maximum pressures change as a function of the pressure administered over the course of a therapy session.

Aspects of at least one of the configurations disclosed herein includes the realization that an AutoPAP system can be configured to not only automatically change the instant pressure delivered to the patient during a therapy session, but additionally to automatically change, at least in one mode of operation, the minimum and/or maximum pressures deliverable by the AutoPAP system.

With reference to FIG. 1, a configuration for a respiratory therapy system 100 is shown. In the illustrated configuration, the respiratory system 100 may comprise a flow generator 101. The flow generator 101 may comprise a gas inlet 102 and a gas outlet 104. The flow generator may comprise a blower 106. The blower 106 may comprise a motor. The motor may comprise a stator and a rotor. The rotor may comprise a shaft. An impeller may be linked to the shaft. In use, the impeller may rotate concurrently with the shaft to draw in gas from the gas inlet 102. The flow generator 101 may comprise a user interface 108 which may comprise one or more buttons, knobs, dials, switches, levers, touch screens, and/or displays so that a user might view data related to the operation of the flow generator 101 or to other components of the respiratory therapy system 100 or input operation parameters into the flow generator 101 to control its operation or the operation of other aspects of the respiratory therapy system 100. The flow generator 101 may pass gas through the gas outlet 104 to a first conduit 110. The first conduit 110 may pass the gas to a humidifier 112 that may entrain moisture in the gas to provide a humidified gas stream. The humidifier 112 may comprise a humidifier inlet 116 and a humidifier outlet 118. The humidifier 112 may comprise a reservoir 114 that may be filled with water or some other humidifying agent. The humidifier 112 may comprise a heating element 113. The heating element 113 may be used to heat the humidifying agent in the reservoir 114 to encourage agent vaporization and/or entrainment in the gas flow and/or increase the temperature of gases passing through the humidifier 112. The humidifier 112 may have a user interface 120 which may comprise one or more buttons, knobs, dials, switches, levers, touch screens, and/or displays so that a user might view data related to the operation of the humidifier 112 or to other components of the respiratory therapy system 100 or input operation parameters into the humidifier 112 to control the operation of the heating element 113, operation of other aspects of the humidifier 112, and/or other aspects of the respiratory therapy system 100. Gas may then pass from the humidifier outlet 118 to a second conduit 122. The second conduit 122 may comprise a heater. The heater may be used to add heat to gases passing through the second conduit 122 in order to prevent the condensation of moisture entrained in the gas stream along the walls of the second conduit 122. The heater may comprise one or more resistive wires located in, on, around or near the walls of second conduit 122. Gas passing through the second conduit 122 may then enter a patient interface 124 that may pneumatically link the respiratory therapy system 100 to the patient's airway. The patient interface 124 may comprise a nasal mask, an oral mask, an oro-nasal mask, a full face mask, a nasal pillows mask, a nasal cannula, an endotracheal tube, a combination of the above or some other gas conveying system. The flow generator 101, humidifier 112, and/or other parts of the respiratory therapy system 100 may comprise a controller (not shown). The controller may be a microprocessor. The controller may help to control the operation of the flow generator 101, humidifier 112, and/or other aspects or operation parameters of the respiratory therapy system 100.

In the illustrated configuration, and as implied above, the respiratory therapy system 100 may operate as follows: gas may be drawn into the flow generator 101 through the gas inlet 102 due to the rotation of an impeller of the motor of the blower 106. Gas may then be propelled out of the gas outlet 104 and along the first conduit 110. The gas flow may enter the humidifier 112 through the humidifier inlet 116. Once in the humidifier 112, the gas may pick up moisture while passing over the humidification agent in the reservoir 114. The humidification agent in the reservoir 114 may be heated by the heating element 113, which may aid in the humidification and/or heating of the gas passing through the humidifier 112. The gas may then leave the humidifier 112 through the humidifier outlet 118 and enter the second conduit 122. Gas may then be passed from the second conduit 122 to the patient interface 124, where it may be taken into the patient's airways to aid in the treatment of respiratory disorders.

It should be understood that the illustrated configuration should not be taken to be limiting, and that many other configurations for the respiratory therapy system 100 are possible. In some configurations, the flow generator 101 may, for example, comprise a source or container of compressed air. The container may comprise a valve that may be adjusted to control the flow of gas leaving the container. In some configurations, the flow generator 101 may use such a source of compressed air or another gas source in lieu of a blower 106. In some configurations the blower 106 may be used in conjunction with another gas source. In some configurations the flow generator 101 may draw in atmospheric gases through the gas inlet 102. In some configurations the flow generator 101 may be adapted to both draw in atmospheric gases through the gas inlet 102 and accept other gases (e.g. oxygen, nitric oxide, carbon dioxide, etc.) through the same inlet 102 or a different inlet. In some configurations the humidifier 112 can be integrated with the flow generator 101. In some configurations the humidifier 112 and the flow generator 101 may share a housing. In some such configurations only a single conduit extending between the flow generator 101 and the patient interface 124 need be used to convey gases to a patient. In some configurations, the humidifier 112 may not be present. In some such configurations, the first conduit 110 and the second conduit 122 may be replaced with a single conduit extending from the flow generator 101 to the patient interface 124. In some configurations, the flow generator 101 and the humidifier 112 may have a single user interface located on either the flow generator 101 or the humidifier 112. In some configurations, the operation of the flow generator 101, of the humidifier 112, or of other aspects of the respiratory therapy system 100 may be controlled a single controller. In some configurations, the operation of the flow generator 101, of the humidifier 112, or of other aspects of the respiratory therapy system 100 may be controlled wirelessly using a user interface located on a remote computing device. In some configurations, the respiratory therapy system 100 may comprise one or more sensors for detecting various characteristics of the gas, including pressure and/or flow rate.

The respiratory therapy system 100 may comprise one or more sensors capable of detecting one or more characteristics of the patient, characteristics of the respiratory activity of the patient, characteristics of the respiratory therapy system 100, data related to the operation of the respiratory therapy system 100, and/or characteristics of gases moving through the respiratory therapy system 100. The one or more sensors may include one or more of the following: a pressure sensor, a flow sensor, a sound sensor, a motor current transducer, a motor speed transducer, a motor torque transducer, a heart rate sensor, a plethysmograph, an electroencephalograph (EEG), an electrocardiograma motion sensor, a breath composition sensor, a pulse oximeter, a blood oxygen concentration sensor, and a blood CO2 concentration sensor. The characteristics obtainable from the one or more sensors may include one or more of the following: gas pressure, gas flow, sound, flow generator motor current, flow generator motor speed, flow generator motor torque, heart rate, tidal volume, lung volume, EEG signal, ECG signal, movement, breath composition, blood oxygen concentration, and blood CO2 concentration. The one or more sensors may be physically part of the respiratory therapy system 100 or wired to a part of the respiratory therapy system 100. In some configurations, the one or more sensors may be remote from the respiratory therapy system 100. The one or more sensors may be capable of wireless communication with the respiratory therapy system 100. Measurements obtained by the one or more sensors of the respiratory therapy system 100 may be used to determine, for example, a trait of a sleep-disordered breathing event (SDBE) of a patient using the respiratory therapy system 100. A controller of the respiratory therapy system 100, which may be, for example, a microprocessor, may use the characteristics obtained by the one or more sensors to determine a trait of the SDBE. The controller of the respiratory therapy system 100 may be physically part of the respiratory therapy system 100 or wired to a part of the respiratory therapy system 100. In some configurations, the controller may be remote from the respiratory therapy system 100, e.g., on a remote server or a mobile device (e.g., a tablet or cellular phone). The controller may be capable of wireless communication with the respiratory therapy system 100. Determined traits of the SDBE may include the presence, absence, type, severity, and/or length of the SDBE. The type of an SDBE may include one or more of the following: an apnea, a hypopnea, and a flow limitation. The severity of an SDBE may be a numerical indicator or may be a qualitative designation that may be applied to a particular SDBE, e.g. 'mild,' 'moderate,' or 'severe.' In some cases, an SDBE may be predicted by the characteristics of the respiratory flow preceding an SDBE. For example, in some cases, an apnea event may be predicted by analysis of the flow waveform of breaths preceding the apnea. One additional trait of an SDBE may be the latency of the SDBE, which may be defined as a function of one or more qualities of the respiratory activity of the patient preceding the SDBE. The qualities may be one or more of a flow waveform, a pressure waveform, motion of the patient, or some other indicator of respiratory activity preceding an SDBE.

Attention is now given to use of a respiratory therapy system 100 configured for use as an AutoPAP device. In such a device, the respiratory therapy system 100 may comprise a controller that, in at least one mode of operation, may define a range of pressures. The range of pressures may be bounded by a minimum pressure level defining the lowest pressure deliverable by respiratory therapy system 100 and/or by a maximum pressure level defining the highest pressure deliverable by the respiratory therapy system 100. The minimum and/or maximum pressures may be the pressures delivered to the patient or pressures taken at any point of the respiratory therapy system 100. The minimum and maximum pressures may be different pressures. The flow generator 101 may be controlled such that the respiratory therapy system 100 may deliver a pressure to the patient that is no less than the minimum pressure level and no greater than the maximum pressure level. The AutoPAP device may be configured to detect one or more traits of an SDBE experienced by a patient during a therapy session and respond by maintaining or adjusting the pressure delivered by the respiratory therapy system 100 based on the traits to accommodate the therapy and/or comfort needs of the patient. For example, upon detecting that the patient is experiencing an episode of obstructive sleep apnea, the respiratory therapy system 100 may increase the pressure delivered to compensate for the apnea episode. Similarly, upon detecting the absence of an SDBE for a period of time, the respiratory therapy system 100 may decrease the pressure delivered to improve the comfort of the therapy for the patient. In some configurations, BiPAP therapy may be used in conjunction with AutoPAP therapy. In some such configurations, the therapeutic pressure (e.g. the instant pressure delivered during AutoPAP therapy) may be the pressure used during patient inhalation, and the pressure may be lowered upon patient exhalation. In some configurations, the therapeutic pressure delivered may be the pressure used during patient exhalation, and the pressure may be increased upon patient inhalation. In some configurations, the EPAP may not be less than the minimum pressure. In some configurations, the IPAP may not be greater than the maximum pressure.

Several methods of automatically adjusting the minimum and maximum pressures of an AutoPAP device are described herein. With reference to FIG. 4, a pair of graphs showing pressure versus time depict a method for adjusting the minimum and maximum pressures of an AutoPAP device. On the left graph, a therapy session (hereinafter referred to as the 'current' therapy session) in which AutoPAP therapy is used is shown. As can be observed, the session may begin with the device delivering the minimum pressure (although in some configurations, other starting pressures may be used), and the pressure delivered may gradually increase and decrease as the patient experiences apneas, hypopneas, or other SDBEs, or the absence of SDBEs, or other conditions warranting a pressure adjustment. The device may record data indicative of the pressures delivered over the course of the current therapy session. In some configurations, during or after the current therapy session, the device may analyze the data recorded over the current therapy session and/or the data recorded over one or more past therapy sessions. The data recorded may be used to determine a target pressure $P_t$ which the patient spent at least an amount of time T at or under. In this example, the amount of time T is predetermined to be at least 90% of the total time of the current therapy session. However, the amount of time could be at least a predetermined number of hours (e.g., 3 hours, 10 hours, 20 hours, 30 hours, etc.), another percentage of the therapy session (e.g., at least 95% of the total time, at least 85% of the total time, at least 80% of the total time, at least 75% of the total time, etc.), a percentage of one or more past therapy sessions (e.g., at least 95% of past therapy sessions, at least 85% of past therapy sessions, at least 80% of past therapy sessions, at least 75% of past therapy sessions, etc.), a variable amount of time determined as a function of other variables of the current or past sessions of use, or a combination of the above. In some configurations, the device may determine a target pressure $P_t$ at or under which the patient spent at least an amount of time T, where the time T may be an average of times spent over the course of multiple therapy sessions or periods of time. For example, the amount of time T may be predetermined to be an average of at least 90% of the total time of the current therapy session and the last two previous sessions. In such an example, if all of the therapy sessions are 8 hours in length, and the patient spends 85% of the first previous session at or under the target pressure $P_t$, 90% of the second previous session at or under the target pressure $P_t$, and 95% of the current session at or under the target pressure $P_t$, the average amount of time T which the patient spends at or under the target pressure $P_t$ may be determined to be 90%. This target pressure $P_t$ may be considered a pressure which is therapeutically effective for the patient. The minimum and maximum pressures may be adjusted to a function of the target pressure $P_t$. In some configurations, the minimum and/or maximum pressures may be changed to the target pressure $P_t$ minus and/or plus a pressure offset $P_o$, respectively. The pressure offset $P_o$ may be predetermined or may be a function of the target pressure $P_t$ or of some other variable. In some configurations, multiple pressure offsets may be used—for example, a minimum pressure offset $P_{o\_min}$ may be used to calculate the minimum pressure from the target pressure $P_t$ and a maximum pressure offset $P_{o\_max}$ may be used to calculate the maximum pressure from the target pressure $P_t$. In the illustrated example, the target pressure $P_t$ at which the patient spent 90% of the therapy session at or under was calculated to be 10 cm $H_2O$. The pressure offset $P_o$ was predetermined to be 2 cm $H_2O$. Correspondingly, as can be seen on the right graph, the minimum pressure has been changed to 8 cm $H_2O$ (10 cm $H_2O$−2 cm $H_2O$) and the maximum pressure has been changed to 12 cm $H_2O$ (10 cm $H_2O$+2 cm $H_2O$). This new pressure range (8 to 12 cm $H_2O$) may be used for subsequent therapy sessions, and may be more therapeutically effective for the patient than the original pressure range (4 to 18 cm $H_2O$) while still allowing some improved flexibility and comfort over traditional constant PAP therapy.

In some configurations, constant PAP therapy may be used for several periods of time, and a target pressure $P_t$ may be determined after analyzing data recorded during these periods of time. A period of time may be a number of seconds, a number of minutes, a number of hours, a number of days, a therapy session, a number of therapy sessions, a percentage of a therapy session, or some other quantity of time. In some such configurations, a PAP device may be used (which may be the AutoPAP device or some other PAP device) to administer constant PAP therapy over the course of several periods of time. The individual time periods may be successive or may be staggered (e.g., non-successive). The pressure delivered during the individual time periods may be different such that different measurements relating to the traits of SDBEs or quality of sleep over the course of each individual time period may be obtained. In some configurations, a sleep index $S_i$ may be determined indicating some aspect of the SDBE traits determined over the course of a time period. The sleep index $S_i$ may, for example, be an apnea-hypopnea index (AHI), total apnea event count, total hypopnea event count, total flow limitation event count, a combination of some or all of the above, or some other value. In some configurations, a sleep quality index $SQ_i$ may be determined indicating a value derived from a function of one or more sleep indices $S_i$. The determined sleep quality index $SQ_i$ may comprise a numeral indicator quantifying the perceived sleep quality for a given time period. In some such configurations, higher sleep quality indices $SQ_i$ indicate high sleep qualities. The sleep index/indices $S_i$ and/or the sleep quality index/indices $SQ_i$ obtained for each individual time period may be compared with each other at the end of the several periods of time. For example, the lowest sleep index $S_i$ and/or highest sleep quality index $SQ_i$ among the set of sleep indices or sleep quality indices $SQ_i$ found for the several periods of time may be determined. The target pressure $P_t$, minimum pressure and/or maximum pressure may then be set to the CPAP pressure used during the period of time at which the lowest sleep index $S_i$ and/or highest sleep quality index $SQ_i$ was found, or a function of the CPAP pressure used during this period of time. In some configurations minimum and/or maximum pressures may be derived from the target pressure $P_t$, and AutoPAP therapy can be utilized based on the therapy range established. This may be actuated by using one or more offset pressures $P_o$ as described herein.

To demonstrate the above, attention is now given to FIGS. 8A-8D. In the illustrated configuration, the several time periods may be several therapy sessions. In FIG. 8A, constant PAP therapy at a pressure of 8 cm $H_2O$ is used for a first therapy session. In FIG. 8B, constant PAP therapy at a pressure of 10 cm $H_2O$ is used for a second therapy session. In FIG. 8C, constant PAP therapy at a pressure of 12 cm $H_2O$ is used for a third therapy session. In FIG. 8D, constant PAP therapy at a pressure of 14 cm $H_2O$ is used for a fourth therapy session. An apnea-hypopnea index (AHI) may be calculated for each individual therapy session and a target pressure $P_o$ may be set to the CPAP pressure used during the therapy session on which the lowest AHI was recorded. In the illustrated configuration, an AHI of 30/hour was obtained for the first therapy session, an AHI of 20/hour was obtained for the second therapy session, an AHI of 7/hour was obtained for the third therapy session, and an AHI of 5/hour was obtained for the fourth therapy session. The AHI of 5/hour for the fourth therapy session was the lowest AHI recorded over the course of the several therapy sessions, and so the target pressure $P_t$ may be set to 14 cm $H_2O$. A pressure offset $P_o$ may be used to determine a minimum pressure and/or a maximum pressure. For example, if the pressure offset $P_o$ is predetermined to be 2 cm H2O, then the minimum pressure may be set to (14 cm $H_2O$−2 cm $H_2O$) or 12 cm $H_2O$ and the maximum pressure may be set to (14 cm $H_2O$+2 cm $H_2O$) or 16 cm $H_2O$. For the fifth and/or other future therapy sessions, instead of constant PAP therapy, AutoPAP therapy may be used with a minimum pressure of 12 cm $H_2O$ and a maximum pressure of 16 cm $H_2O$. The minimum and maximum ranges thereon may be changed through the use of other methods identical or similar to those disclosed herein. In other configurations a predetermined AHI value may be established and the target pressure $P_o$ may be set to the lowest CPAP pressure for which the calculated AHI was less than or equal to the predetermined AHI value or a function of the lowest CPAP pressure. In other configurations the minimum and/or maximum pressures may be set to some other function of the target pressure $P_o$.

Figure 9:
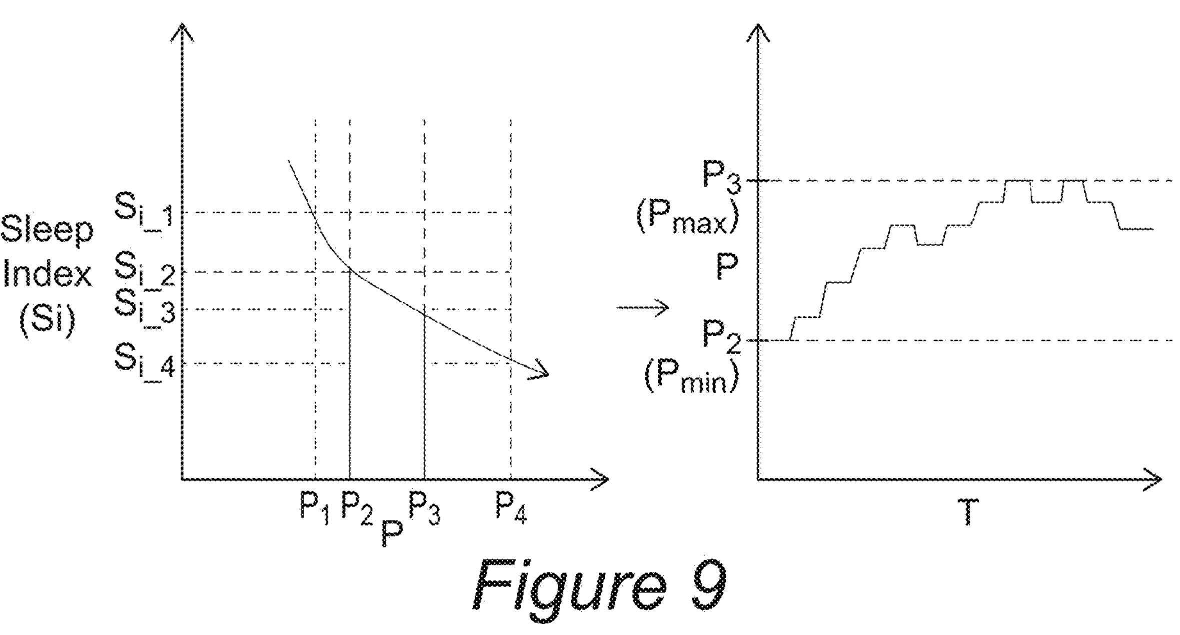
FIG. 9 shows a method for selecting minimum and/or maximum pressures for AutoPAP therapy based on a set of pressures used in several sessions of constant PAP therapy.
Figure 10:
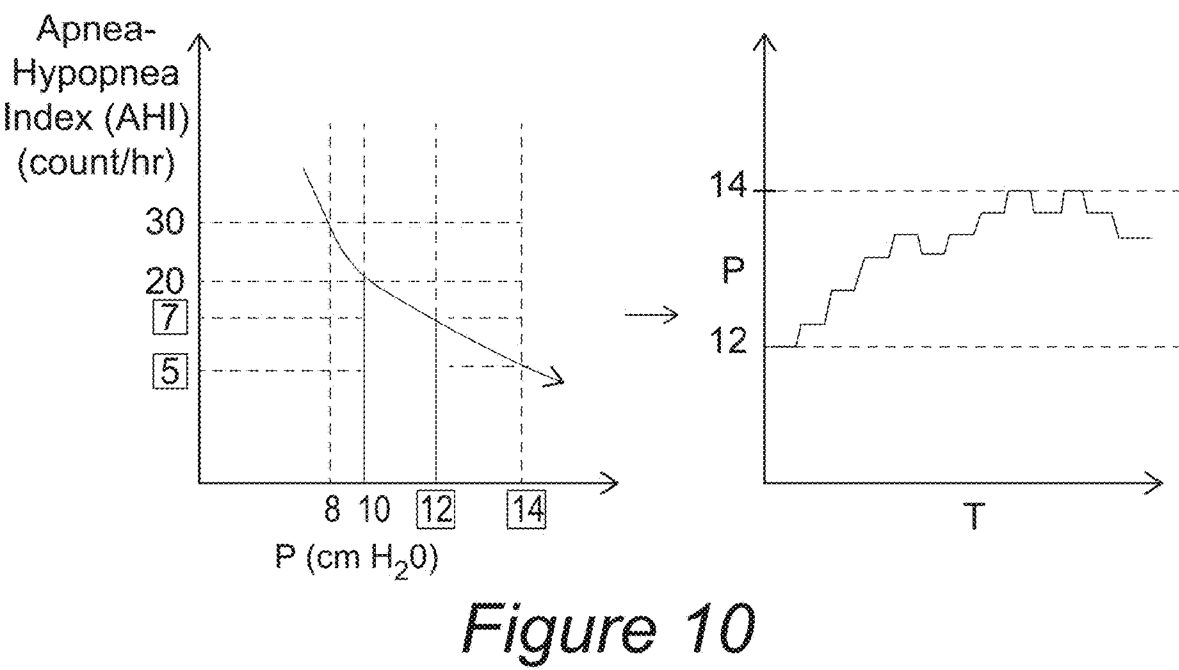
FIG. 10 shows a relationship between constant PAP pressures and AHI values.

In some configurations, the minimum and/or maximum pressures may be selected based on a range of sleep indices $S_i$ and/or sleep quality indices $SQ_i$. With continued reference to FIGS. 8A-8D, constant PAP therapy may be used for several therapy sessions, wherein a different constant PAP pressure may be used for each individual therapy session. Similarly, sleep indices $S_i$ and/or sleep quality indices $SQ_i$ may be calculated for each individual therapy session. FIG. 9 demonstrates a pressure versus sleep index $S_i$ function, although it should be understood that a similar graph may be used to illustrate a pressure versus sleep quality index $SQ_i$ function. As shown in FIG. 9, a relationship between the sleep indices $S_i$ and/or sleep quality indices $SQ_i$ and the CPAP pressures used may be found. The sleep indices $S_i$ and/or sleep quality indices $SQ_i$ may be plotted against the CPAP pressures used. A polynomial function may be found describing the relationship between the sleep indices $S_i$ and/or sleep quality indices $SQ_i$ and the CPAP pressures used. In some configurations, a range of sleep indices $S_i$ bounded by a minimum sleep index value $S_{i\_min}$ and a maximum sleep index value $S_{i\_max}$ may be defined. The range may be predetermined. The minimum sleep index value $S_{i\_min}$ may designate a first predetermined sleep index value where gas therapies resulting in sleep index values under the first predetermined sleep index value are considered sub-optimal. The maximum sleep index value $S_{i\_max}$ may designate a second predetermined sleep index value where gas therapies resulting in sleep index values over the second predetermined sleep index value are considered sub-optimal. Minimum and/or maximum pressures may be determined from analysis of the polynomial function by determining a minimum pressure at which a minimum sleep index $S_{i\_min}$ may be observed and/or a maximum pressure at which a maximum sleep index $S_{i\_max}$ may be observed. As an example, as seen in FIGS. 8A-8D, four sessions of therapy may be recorded in which different constant PAP pressures (in this case, 8 cm $H_2O$ for the first session, 10 cm $H_2O$ for the second session, 12 cm $H_2O$ for the third session, and 14 cm $H_2O$ for the fourth session) are used and different AHI values (the sleep indices $S_i$ in this case) may be obtained for each session (in this case, AHI values of 30/hour for the first session, 20/hour for the second session, 7/hour for the third session, and 5/hour for the fourth session). As seen in FIG. 10, the relationship between the constant PAP pressures used and the AHI values obtained may be plotted. A polynomial function showing the AHI as a function of the CPAP pressure used may be found, and the pressures corresponding to the minimum AHI value and/or the maximum AHI value may be found. In this example, and as demonstrated by FIGS. 8A-8D and FIG. 10, the minimum AHI value was predetermined to be 5/hour and the maximum AHI value was predetermined to be 7/hour. The pressures corresponding to the minimum and maximum AHI values were found to be 14 cm $H_2O$ and 12 cm $H_2O$, respectively. In this example, AutoPAP therapy may then be used, where 12 cm $H_2O$ may be assigned as the minimum pressure and 14 cm $H_2O$ may be assigned as the maximum pressure.

Figure 5:
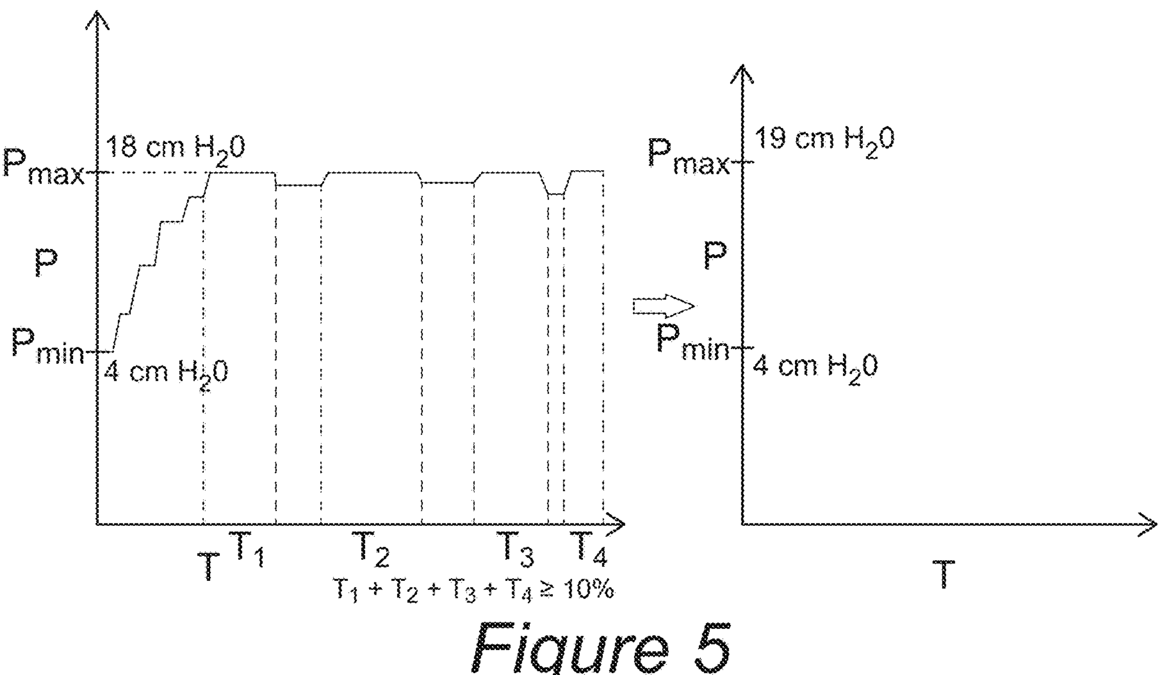
FIG. 5 shows a pair of pressure versus time graphs demonstrating an example of AutoPAP therapy wherein the maximum pressure increases relative to the time spent delivering the maximum pressure.

In some configurations, if the maximum pressure deliverable is determined to be too low, the AutoPAP device may automatically increase the maximum pressure. With reference to FIG. 5, a pair of pressure versus time graphs depicting a method for adjusting the maximum pressure for an AutoPAP device is shown. On the left graph, a therapy session in which AutoPAP is used is shown. As can be observed, the session may begin at the minimum pressure (but may begin at some other pressure) and may increase to a higher pressure upon detecting apneas, hypopneas, or other SDBEs. The pressure may increase to the maximum pressure. After or over the course of a monitoring period (which may be a number of hours, a portion of a therapy session, an entire therapy session, multiple therapy sessions, or some other period of time), the amount of time $T_{max\_total}$ over which the device delivers the maximum deliverable pressure may be calculated or monitored. If the $T_{max\_total}$ is determined to be greater than or equal to a threshold percentage T % of the monitoring period, the device may increase the maximum deliverable pressure. The maximum pressure may be adjusted, for example, immediately after the determination, a period of time after the determination, or during a subsequent therapy session. In the illustrated example, the $T_{max\_total}$ (here, $T_1+T_2+T_3+T_4$) was found to be 50% of the monitoring period, the T % was predetermined to be 10% of the monitoring period, and the monitoring period was predetermined to be an entire therapy session. The $T_{max\_total}$ was determined to be greater than the T %, and so the maximum pressure 18 cm $H_2O$ was increased to 19 cm $H_2O$. In some configurations, the maximum pressure may increase by a predetermined amount, by a predetermined amount up to a limit, by a function of the current maximum pressure, by a function of the current minimum pressure, and/or by a function of the number and/or intensity of previous maximum and/or minimum pressure changes. In the illustrated example, the new maximum pressure could be used in a subsequent therapy session.

Figure 6:
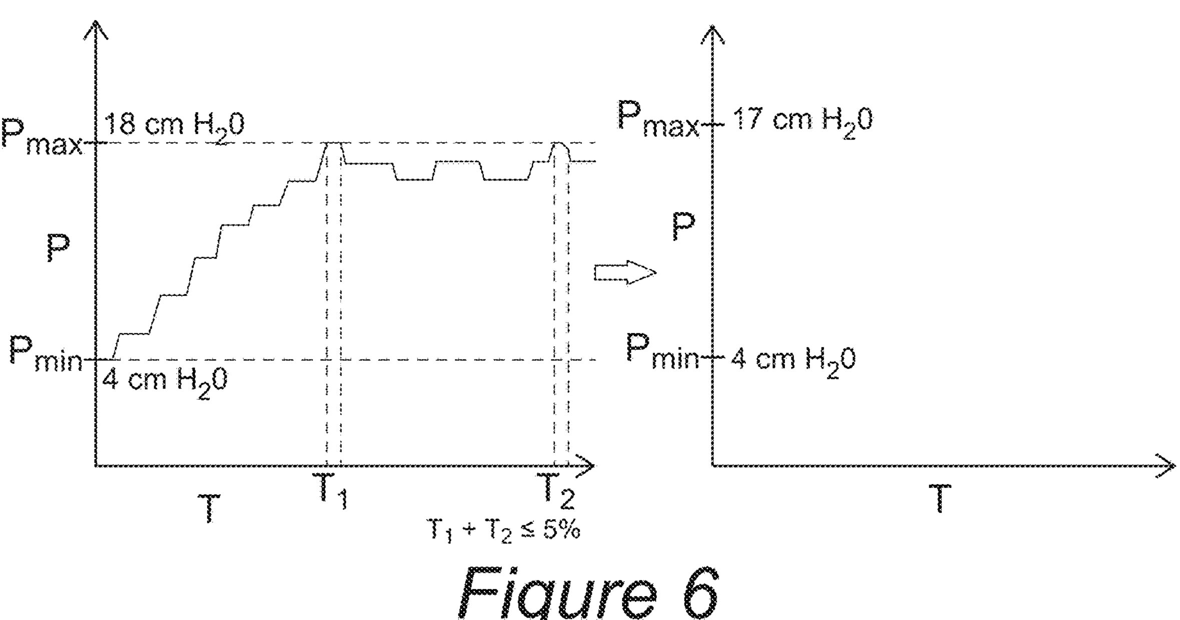
FIG. 6 shows a pair of pressure versus time graphs demonstrating an example of AutoPAP therapy wherein the maximum pressure decreases relative to the time spent delivering the maximum pressure.

Similarly, in some configurations, if the maximum pressure deliverable is determined to be too high, the AutoPAP device may automatically decrease the maximum pressure. With reference to FIG. 6, a pair of pressure versus time graphs depicting a method for adjusting the maximum pressure for an AutoPAP device is shown. On the left graph, a therapy session in which AutoPAP is used is shown. As can be observed, the session begins at the minimum pressure and may increase to the pressure upon detecting apneas, hypopneas, or other SDBEs. The pressure may increase to the maximum pressure. After or over the course of a monitoring period (which may be a number of hours, a portion of a therapy session, an entire therapy session, multiple therapy sessions, or some other period of time), the amount of time $T_{max\_total}$ over which the device delivers the maximum deliverable pressure may be calculated or monitored. If the $T_{max\_total}$ is determined to be less than or equal to a threshold percentage T % of the monitoring period, the device may decrease the maximum deliverable pressure. The maximum pressure may be adjusted, for example, immediately after the determination, a period of time after the determination, or during a subsequent therapy session. In the illustrated example, the $T_{max\_total}$ (here, $T_1+T_2$) was found to be 4% of the monitoring period, the T % was predetermined to be 5% of the monitoring period, and the monitoring period was predetermined to be an entire therapy session. The $T_{max\_total}$ was determined to be less than the T %, and so the maximum pressure 18 cm $H_2O$ was decreased to 17 cm $H_2O$. In some configurations, the maximum pressure can decrease by a predetermined amount, by a predetermined amount up to a limit, by a function of the current maximum pressure, by a function of the current minimum pressure, and/or by a function of the number and/or intensity of previous maximum and/or minimum pressure changes. In the illustrated example, the new maximum pressure could be used in a subsequent therapy session.

Figure 7:
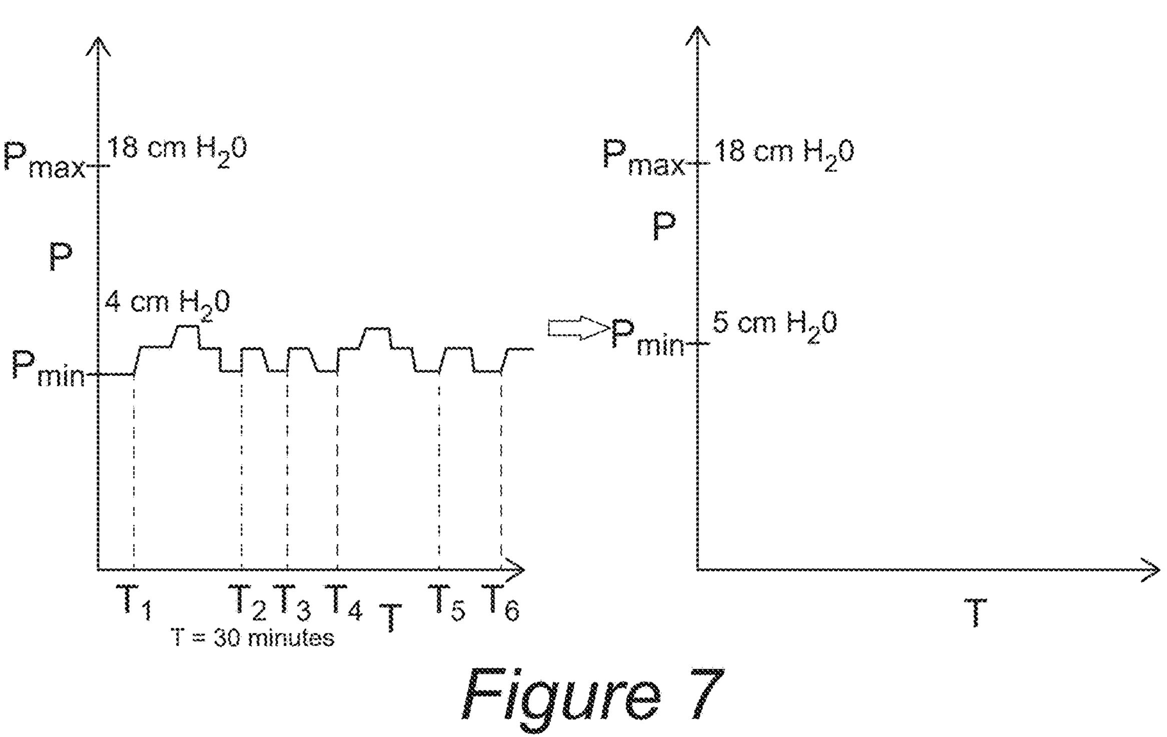
FIG. 7 shows a pair of pressure versus time graphs demonstrating an example of AutoPAP therapy wherein the minimum pressure increases as a function of the frequency of events occurring at the minimum pressure.

In some configurations, if the minimum pressure deliverable is determined to be too low, the AutoPAP device may automatically increase the minimum pressure. With reference to FIG. 7, a pair of pressure versus time graphs depicting a method for adjusting the minimum pressure for an AutoPAP device is shown. On the left graph, a therapy session in which AutoPAP is used is shown. As can be observed, the session begins at the minimum pressure (but may begin at some other pressure) and the pressure delivered gradually increases and decreases as the patient experiences apneas, hypopneas, or other SDBEs or the absence of SDBEs, or other conditions warranting a pressure adjustment. If the device determines that a significant number of pressure-increasing SDBEs or other conditions warranting a pressure increase have occurred at or near the minimum pressure, the minimum pressure may be determined to be too low. For example, the device may define an event count $E_c$ representing a number of pressure increases occurring at or near (e.g., within 1 to 3 cm H2O) the minimum pressure, an event count threshold $E_{c\_t}$ and a predetermined time Tp. If the event count $E_c$ over a defined time $T_p$ is greater than an event count threshold $E_{c\_t}$, the device may increase the minimum pressure. In the illustrated example, the $T_p$ was defined to be 30 minutes, the $E_c$ was found to be 6 (see T1-T6 on left graph), and the $E_{c\_t}$ was defined to be 5. The $E_c$ for the time $T_p$ was determined to be greater than the $E_{c\_t}$, so the minimum pressure was raised from 4 cm $H_2O$ to 5 cm $H_2O$. Similarly, the minimum pressure may be adjusted, for example, after the determination, a period of time after the determination, or during a subsequent therapy session. In some configurations, the minimum pressure can increase by a predetermined amount, by a predetermined amount up to a limit, by a function of the current maximum pressure, by a function of the current minimum pressure, and/or by a function of the number and/or intensity of previous maximum and/or minimum pressure changes. In the illustrated configuration, the new minimum pressure may be used in a subsequent therapy session.

Figure 11:
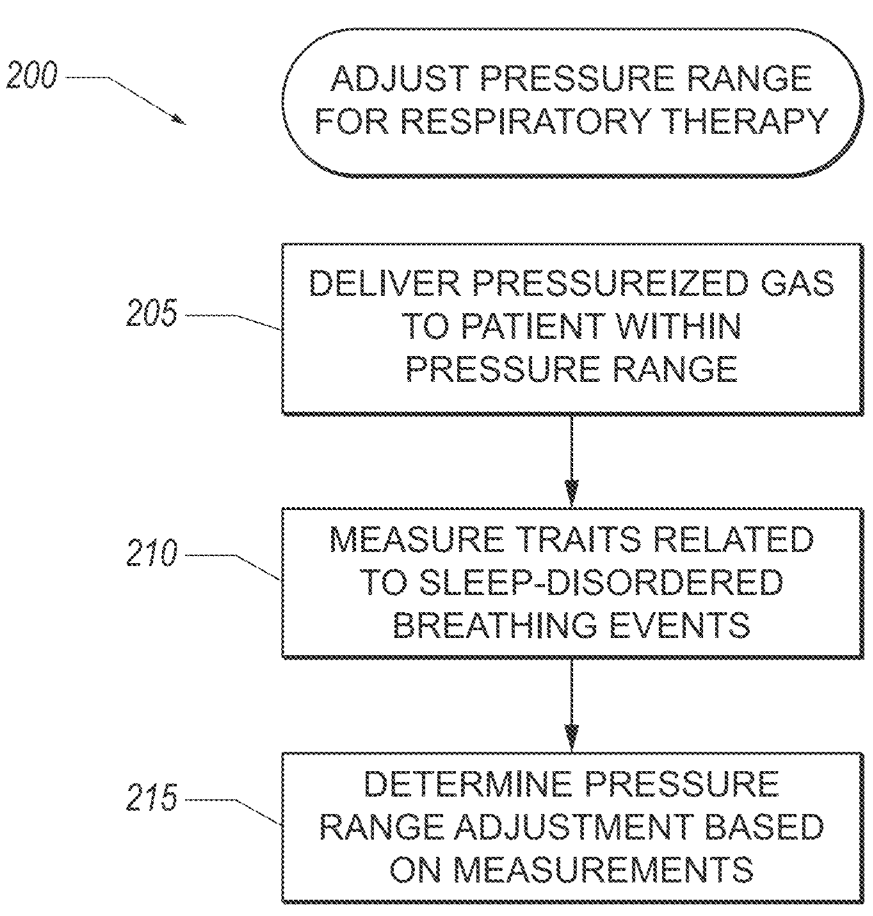
FIG. 11 shows a flow chart of an example method for adjusting a pressure range for respiratory therapy.

FIG. 11 illustrates a flow chart of an example method 200 for adjusting a pressure range for respiratory therapy using an AutoPAP device. The method can be implemented by the devices described herein or by any other suitable AutoPAP device configured to deliver automatically adjusting pressure during respiratory therapy. The method 200 can be used to adjust minimum and/or maximum pressures available to the AutoPAP device when providing respiratory therapy. In some embodiments, the method 200 can be implemented by one or more software and/or hardware components on the AutoPAP device. For ease of description, then, the method 200 will be described as being performed by an AutoPAP device. However, any other suitable configuration of modules, devices, apparatuses, and systems comprising software and/or hardware can be used to implement one or more steps of the method 200.

In block 205, the AutoPAP device delivers pressurized gas to a patient, the pressurized gas having a pressure within an initial pressure range. The minimum and/or maximum pressures can be, for example and without limitation, set by a user, a physician, a clinician, or the pressures can be default values of the AutoPAP device. In some embodiments, the AutoPAP device limits the potential values of the minimum and/or maximum pressures available during respiratory therapy. For example, the AutoPAP device can be configured to not allow a minimum pressure limit to be below 4 cm $H_2O$. As another example, the AutoPAP device can be configured to not allow a maximum pressure limit to exceed 20 cm $H_2O$. Thus, if one or more conditions of the patient (e.g., the presence or absence of SDBEs) indicate that the minimum and/or maximum pressure available for therapy should change, the AutoPAP device can leave one or both of the pressure limits unchanged if the change would result in a pressure limit setting that is outside of the defined allowable limits.

In block 210, the AutoPAP device measures at least one characteristic capable of being used to determine one or more traits of a sleep-disordered breathing event (SDBE), as described elsewhere herein. The at least one characteristic may be analyzed to determine the one or more traits of a sleep-disordered breathing event of the patient, as described elsewhere herein.

In block 215, the AutoPAP device analyzes the traits of a sleep-disordered breathing event of the patient to determine whether to change the pressure range limits. As described herein, the AutoPAP device can use measured information from the current therapy session to make this determination. Similarly, the AutoPAP device can use measured data from previous therapy sessions to make this determination. Moreover, the AutoPAP device can use measured data from the current therapy session in combination with one or more previous therapy sessions or portions of one or more previous therapy sessions to make this determination. In some embodiments, the AutoPAP device makes this determination on an event-by-event basis.

In this manner, the AutoPAP device can use the method 200 to automatically limit the range of pressures used during respiratory therapy. This can lead to greater efficacy in respiratory therapy, greater patient compliance, and improved results relative to other AutoPAP devices that do not adjust the pressure range limits in the manners set forth herein.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The disclosed methods, media, apparatus and systems may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavor in any country in the world.

Certain features, aspects and advantages of some configurations of the present disclosure have been described with reference to use by a patient or user. However, certain features, aspects and advantages of the use of the respiratory therapy system as described may be advantageously practiced by other people on behalf of the patient, including medical professionals, medical device dealers, or medical device providers. Certain features, aspects and advantages of the methods and apparatus of the present disclosure may be equally applied to usage by other people.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A respiratory therapy system comprising:

a flow generator adapted to provide pressurized gases to a patient, a sensor adapted to measure at least one characteristic capable of being used to determine one or more traits of a sleep-disordered breathing event (SDBE) of the patient, and a hardware controller configured to:

receive the at least one characteristic measured by the sensor, determine the one or more traits of the SDBE of the patient by analyzing the at least one characteristic, control the flow generator to deliver pressurized gases, the pressure of the pressurized gases being at least in part based on the determined one or more traits of the SDBE, and the pressure of the pressurized gases being within a delivered gas pressure window comprising a minimum pressure limit and a maximum pressure limit; and repeatedly maintain or adjust the delivered gas pressure window as a function of parameters measured during a course of a therapy session or one or more previous therapy sessions; wherein when the patient spends a percentage of time at the maximum pressure limit that is greater than or equal to a threshold percentage of time at the maximum pressure limit over the course of the therapy session or the one or more previous therapy sessions, the maximum pressure limit is increased.

2. The respiratory therapy system of claim 1, wherein the maximum pressure limit is adjusted during the course of a therapy session.

3. The respiratory therapy system of claim 1, wherein the minimum pressure limit is adjusted during the course of a therapy session.

4. The respiratory therapy system of claim 1, wherein both the minimum pressure limit and the maximum pressure limit are adjusted during the therapy session.

5. The respiratory therapy system of claim 1, wherein the therapy sessions comprise only a current therapy session.

6. The respiratory therapy system of claim 1, wherein the therapy sessions comprise only one or more previous therapy sessions.

7. The respiratory therapy system of claim 1, wherein the therapy sessions comprise both the therapy session and one or more previous therapy sessions.

8. The respiratory therapy system of claim 1, wherein the parameters measured during at least one of the course of the therapy session and one or more previous therapy sessions comprises a percentage of time of one or more sessions over which pressure delivered to patient is at the maximum pressure limit, minus and/or plus a pressure.

9. The respiratory therapy system of claim 8, wherein if the patient experiences a number of delivered pressure increases greater than a predetermined number over a predetermined period of time at or near the minimum pressure limit, the minimum pressure limit is increased.

10. The respiratory therapy system of claim 1, wherein the controller may make a decision to maintain or adjust the minimum pressure limit or the maximum pressure limit on an event-by-event basis.

11. A respiratory therapy system comprising:

a flow generator adapted to provide pressurized gases to a patient, a sensor adapted to measure at least one characteristic capable of being used to determine one or more traits of a sleep-disordered breathing event (SDBE) of the patient, and a hardware controller configured to:

receive the at least one characteristic measured by the sensor, determine the one or more traits of the SDBE of the patient by analyzing the at least one characteristic, control the flow generator to deliver pressurized gases, the pressure of the pressurized gases being at least in part based on the determined one or more traits of the SDBE, and the pressure of the pressurized gases being within a delivered gas pressure window comprising a minimum pressure limit and a maximum pressure limit; and repeatedly maintain or adjust the delivered gas pressure window as a function of parameters measured during a course of a therapy session or one or more previous therapy sessions; wherein when the patient spends a percentage of time at the maximum pressure limit that is less than or equal to a threshold percentage of time at the maximum pressure limit over the course of the therapy session or the one or more previous therapy sessions, the maximum pressure limit is decreased.

12. The respiratory therapy system of claim 11, wherein the maximum pressure limit is adjusted during the course of a therapy session.

13. The respiratory therapy system of claim 11, wherein the minimum pressure limit is adjusted during the course of a therapy session.

14. The respiratory therapy system of claim 11, wherein both the minimum pressure limit and the maximum pressure limit are adjusted during the therapy session.

15. The respiratory therapy system of claim 11, wherein the therapy sessions comprise only a current therapy session.

16. The respiratory therapy system of claim 11, wherein the therapy sessions comprise only one or more previous therapy sessions.

17. The respiratory therapy system of claim 11, wherein the therapy sessions comprise both the therapy session and one or more previous therapy sessions.

18. The respiratory therapy system of claim 11, wherein the parameters measured during at least one of the course of the therapy session and one or more previous therapy sessions comprises a percentage of time of one or more sessions over which pressure delivered to patient is at the maximum pressure limit, minus and/or plus a pressure.

19. The respiratory therapy system of claim 18, wherein if the patient experiences a number of delivered pressure increases greater than a predetermined number over a predetermined period of time at or near the minimum pressure limit, the minimum pressure limit is increased.

20. The respiratory therapy system of claim 11, wherein the controller may make a decision to maintain or adjust the minimum pressure limit or the maximum pressure limit on an event-by-event basis.

* * * * *